(12) United States Patent
Cheng et al.

(10) Patent No.: US 6,768,099 B1
(45) Date of Patent: Jul. 27, 2004

(54) DEVICE FOR DETECTING A PARAMETER ASSOCIATED WITH THE STATE OF A VEHICLE, ESPECIALLY AN AUTOMOBILE

(75) Inventors: Thierry Cheng, Guyancourt (FR); Jean-Luc Auge, Harlow (GB); Antoine De Monts, Cambremer (FR); Patrice Laurent, Swansea (GB)

(73) Assignee: Valeo Climatisation, La Verriere (FR)

( * ) Notice: Subject to any disclaimer, the term of this patent is extended or adjusted under 35 U.S.C. 154(b) by 0 days.

(21) Appl. No.: 09/743,717
(22) PCT Filed: May 18, 2000
(86) PCT No.: PCT/FR00/01353

§ 371 (c)(1),
(2), (4) Date: Mar. 13, 2001

(87) PCT Pub. No.: WO00/69692

PCT Pub. Date: Nov. 23, 2000

(30) Foreign Application Priority Data

May 18, 1999 (FR) .............................. 99 06300

(51) Int. Cl.⁷ ................................................. G02B 6/42
(52) U.S. Cl. ............................. 250/227.24; 250/227.25
(58) Field of Search ..................... 250/227.24, 227.25, 250/573, 574, 221; 340/602, 603, 604

(56) References Cited

U.S. PATENT DOCUMENTS

| | | | | |
|---|---|---|---|---|
| 5,796,106 A | * | 8/1998 | Noack | 250/341.8 |
| 6,052,196 A | * | 4/2000 | Pientka et al. | 356/445 |
| 6,084,519 A | * | 7/2000 | Coulling et al. | 340/602 |
| 6,307,198 B1 | * | 10/2001 | Asakura et al. | 250/227.25 |

FOREIGN PATENT DOCUMENTS

| | | |
|---|---|---|
| DE | 3528009 | 2/1987 |
| DE | 4333665 | 4/1995 |
| EP | 0866330 | 9/1998 |

* cited by examiner

Primary Examiner—Edward J. Glick
Assistant Examiner—Hoon Song
(74) Attorney, Agent, or Firm—Liniak, Berenato & White

(57) ABSTRACT

The invention relates to the detection of parameters that are representative of a state associated with an automobile windscreen (1), by optical means. The inventive device comprises a module (20) that is sensitive to at least one of the aforementioned parameters and which is at least partially embedded in a layer (11) of the windscreen. Said windscreen comprises two glass panels (10a, 10b), which are separated by a spacer comprising the part of the module (20) that is embedded.

32 Claims, 2 Drawing Sheets

Figure 1:
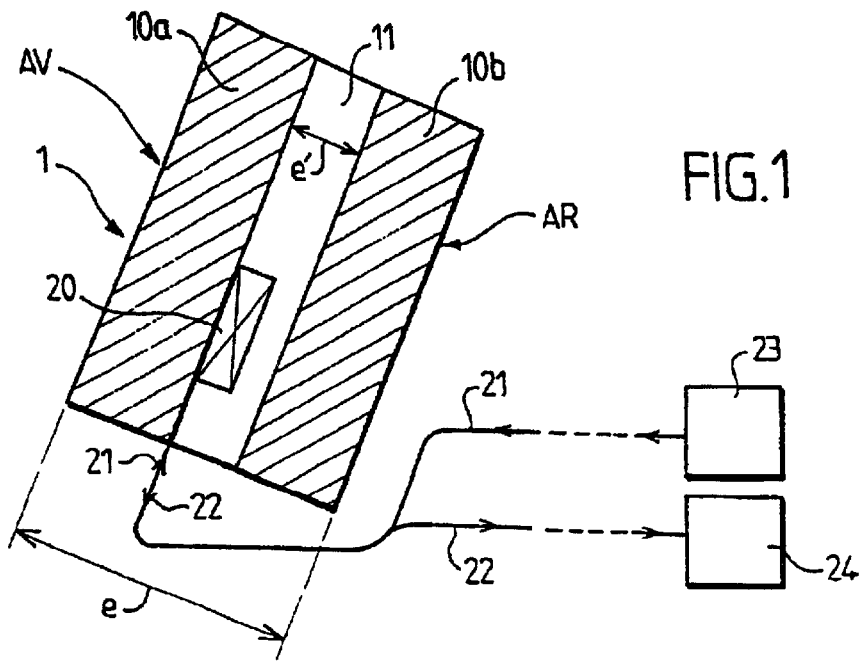

DEVICE FOR DETECTING A PARAMETER ASSOCIATED WITH THE STATE OF A VEHICLE, ESPECIALLY AN AUTOMOBILE

The present invention relates to the field of detection of parameters representative of a state associated with a motor vehicle, in particular the glazing of the vehicle, such as a windscreen or a rear window.

Such a state, associated with the glazing, relates to the presence of misting or of drops of water on one face of the glazing, dirtying or else insolation, which are capable of being detected especially by electromagnetic means.

Known detection devices usually include a module equipped with at least one sensor arranged in the passenger compartment of the vehicle, at a distance from the glazing. That being so, such a sensor does not detect a parameter directly representative of a state associated with the glazing, and it is necessary, in the case of a detection by optical means, to provide shades around this sensor in order to prevent stray light being detected. Moreover, such detection can be disturbed by the presence of smoke in the passenger compartment, as may be the case.

Other known devices include a module equipped with at least one sensor fixed, especially by bonding, on one of the faces of the glazing, on the passenger compartment side. It is then necessary, in this case, to provide shades around the sensor, in particular if it is desired to detect a state associated with the other face of the glazing, on the outside.

The present invention aims to improve the situation.

Moreover, the known devices make it possible only to detect rain on the outer surface of the glazing. The object of the present invention is to provide a device making it possible to detect a foreign body on one or other of the faces of the glazing and especially making it possible to detect both the presence of misting and of rain.

To that end the invention proposes a detection device, including a module sensitive to a parameter representative of a state associated with the glazing, consisting of means (E1) for emitting at least one electromagnetic beam (F1) towards one face (AV) of the glazing, means (R) for receiving at least a part of the beam returned by the said face, and of at least one insert (I1, I2) in the thickness e of the glazing, provided with a surface (S1, S2; S11) substantially opposite the said face (AV, AR) and substantially reflecting to the beam (F1), in such a way that the beam, from emission to reception, undergoes a plurality of reflections in the thickness of the glazing, between the surface (S1, S2; S11) of the insert (I1) and the face (AV, AR) of the glazing.

The implanting of an insert is compatible with the present-day techniques for manufacturing glazing of vehicles, especially windscreens and rear windows, which exhibit a heterogeneous structure generally comprising a spacer thickness between two rigid panels. The reflecting faces of this insert make it possible to detect a foreign substance on one or other of the faces of the glazing.

The receiving means are linked to means for measuring a parameter representative of a proportion of part of a returned beam, this proportion being related to a degree of humidity (drops of water and/or misting) and/or to a degree of dirtying (dust) of the face of the glazing.

Advantageously, moreover, the receiving means are configured so as to detect ambient electromagnetic radiation, while the measuring means are able to distinguish this ambient radiation from a beam part returned by the face of the glazing.

The emitting means preferably include at least one emitting source applied against one of the faces of the glazing.

In a variant, a source of this type is implanted into the thickness of the glazing.

The receiving means preferably include at least one sensor for detecting the beam part returned. This sensor is applied against the face of the abovementioned glazing.

In a variant, a sensor of this type is implanted into the thickness of the glazing.

The emitting means are advantageously configured to emit a first beam intended to be at least partly returned by a front face of the glazing, as well as a second beam intended to be at least partly returned by a rear face of the glazing, with a view to detecting foreign substances on the front and/or rear faces of the glazing.

The measuring means are preferably able to distinguish respective electromagnetic radiation arising from the returns from the first and second beams via the front and rear faces.

The module advantageously includes at least one insert equipped with a first reflecting surface opposite the front face, and with a second reflecting surface opposite the rear face, and the receiving means are configured to receive at least parts of the first and second beams, which are reflected respectively by the front and rear faces.

The emitting means preferably include first and second sources suitable for emitting the first and second beams respectively, while the receiving means include a sensor for detecting the reflected parts of the first and second beams; the first and second sources, as well as the sensor, being applied against the same face of the glazing.

According to one advantageous, optional characteristic, the module of the device further includes a temperature sensor inserted into the thickness of the glazing.

Advantageously, the module includes a luminous-flux sensor, especially a solar-flux sensor, inserted into the thickness of the glazing.

The glazing preferably includes a spacer of chosen thickness, and the module includes a part implanted into a thickness of this spacer.

The present invention also envisages vehicle, especially automobile, glazing, including, in its thickness, an insert of a detection device of the abovementioned type, or else an insert at least a part of the surface of which is intended to be used as a reflecting surface of a detection device of the abovementioned type.

Glazing of this type advantageously comprises two substantially transparent panels, which are substantially rigid and separated by a substantially transparent spacer, into which at least a part of the module of the abovementioned device is inserted.

The insert is preferably substantially in contact with at least one of the panels.

Glazing of this type may advantageously form the windscreen of a motor vehicle, or else the rear window of this vehicle.

Figure 2A:
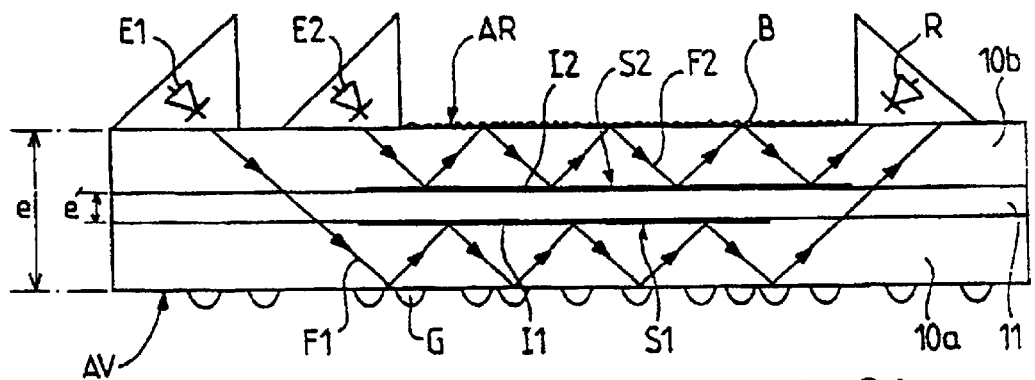
Figure 3A:
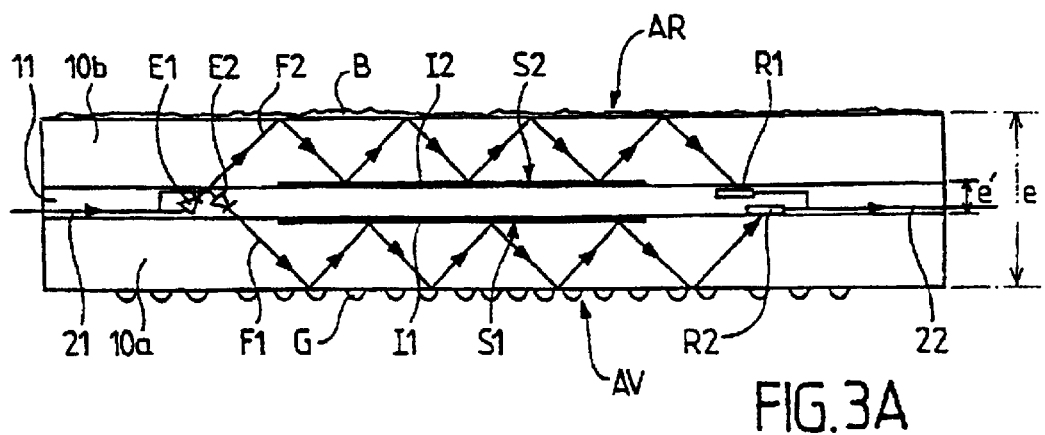
Figure 2B:
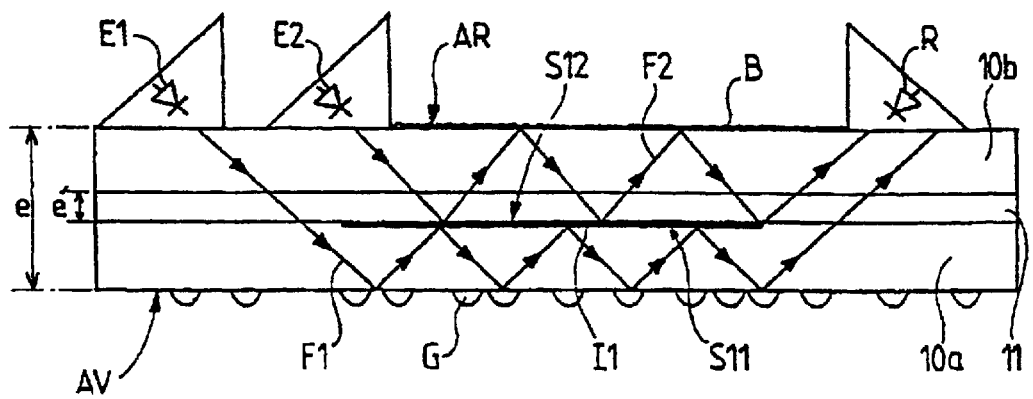
Figure 3B:
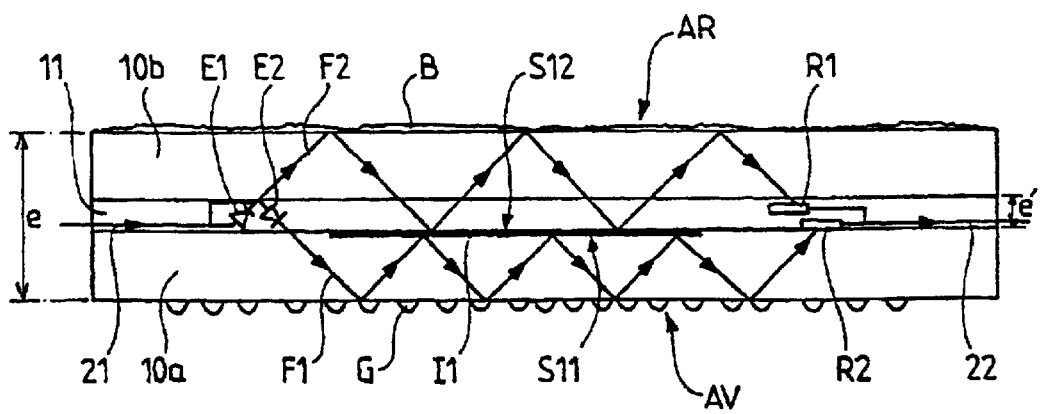

Other advantages and characteristics of the present invention will emerge on reading the detailed description given below by way of example, and the attached drawings, in which:

FIG. 1 diagrammatically represents a detection device according to the invention including a sensor module at least partly implanted into the thickness of motor-vehicle glazing;

FIG. 2A diagrammatically represents a device for detecting a parameter associated with the state of the glazing, in particular its degree of humidity (droplets of water and misting) on the front and rear faces of this glazing, according to a first embodiment;

FIG. 2B represents a variant of the device represented in FIG. 2A with an insert provided with two reflecting surfaces opposite the respective faces of the glazing;

FIG. 3A diagrammatically represents a detection device according to a second embodiment, with emitting means and receiving means implanted into the thickness of the glazing; and FIG. 3B represents a variant of the device represented in FIG. 3A with an insert provided with two reflecting surfaces opposite the respective faces of the glazing.

The detailed description below and the attached drawings contain the essence of the elements of a certain nature. They could therefore not only serve to give a better understanding of the present invention, but also contribute to its definition, as the case may be.

Referring first of all to FIG. 1, a device is described for detecting a parameter representative of the physical state of motor-vehicle glazing 1 of thickness e. According to present-day techniques for manufacturing glazing, in particular motor-vehicle windscreen and rear window, as appropriate, the glazing 1 includes a spacer 11 of thickness e' between two substantially rigid panels 10a and 10b. In the example described, this glazing, intended to form the windscreen of the vehicle, is safety glazing made of laminated material comprising a transparent film of plastic, or more particularly of adhesive, forming a spacer 11 between two glass panels 10a and 10b. The thickness of this spacer film is typically around 0.9 mm.

The detection device according to the invention includes a module 20, at least partly implanted into the thickness e of the glazing 1. In the example represented in FIG. 1, this module 20 is embedded, at least partly, into the spacer film 11.

The module 20 comprises at least one electromagnetic sensor, optical in the example described, preferably in the infrared range. The detection device includes a power supply 23, especially for this sensor, hi linked to the module 20 via a connection 21.

Thus the module, by optical means, detects a parameter representative of a state of the glazing 1, such as its degree of insolation, its degree of humidity (drops of rain on the front face AV of the windscreen, or misting on the rear face AR), or else a degree of dirtying (dust or other). As a consequence of this detection, the module 20 delivers information via the connection 22 to a communications interface 24.

This communications interface 24, in the example described, is linked to an adjusting actuator of equipment of the motor vehicle. Thus, if the module 20 is configured to detect water droplets on the front face AV of the windscreen (outside the vehicle), the communications interface 24 transmits information for the windscreen wiper system, for the purposes of triggering it, as appropriate. If the module 20 detects misting on the rear face AR of the windscreen (passenger compartment side), the communications interface 24 is linked to an actuator for adjusting a heating, ventilation and/or air-conditioning installation, with a view to triggering ventilation for demisting of the windscreen. In a variant according to which the glazing 1 forms the rear window of the vehicle, a communications interface 24 can be linked to the system for de-icing/de-misting of the rear window.

Moreover, if the module 20 is configured to detect insolation of the windscreen, the communications interface 24 is linked to an actuator for adjusting a lighting system which the vehicle includes, for example in order to initiate night lighting below a light threshold detected on the windscreen, as the case may be. Moreover, in the context of night driving, if the module 20 is configured to detect light originating from the headlamps of a vehicle which is following the vehicle including the device according to the invention, the communications interface 24 is linked to an adjusting actuator of a system for shading the rear-view mirrors of the vehicle (achieved by a chosen orientation of crystals which the glazing of the rear-view mirrors includes), in order to prevent the driver being dazzled.

In a first embodiment of the present invention, represented in FIG. 2A, the device including the module 20 is able to detect the presence of drops of water G and of misting B on the front AV and rear AR faces of a windscreen 1 of a motor vehicle. Such a module is then linked via a communications interface 24 with, on the one hand, an adjusting actuator of a wiper system of the vehicle (drops of water G detected) and, on the other hand, with a heating, ventilation and/or air-conditioning installation in order to trigger ventilation of the windscreen (misting B detected).

When the panel 10b has misting B on its face AR (passenger-compartment side of the vehicle), the dioptre which the glass of the panel forms with the water of the misting becomes different from a usual dioptre between the glass of the panel 10b and the surrounding air in the passenger compartment. The coefficient of reflection of this dioptre is altered (reduced, in practice) and, when a beam F2 of predetermined luminous intensity is reflected by the face AR of the panel 10b, the luminous intensity of the beam F2 after reflection varies depending on the quantity of misting present on the face AR of the windscreen.

Likewise, the luminous intensity of a beam F1, after reflection on the front face AV of the windscreen, varies depending on the density of water droplets G.

The module 20 of a device for detecting droplets of rain and misting on the front and rear faces respectively of a windscreen, according to the first above-mentioned embodiment, includes:

a first diode E1, emitting a first light beam F1, intended to be reflected by the front face AV of the windscreen, a second emitting diode E2, delivering a second light beam F2, intended to be reflected by the rear face AR of the windscreen, and a receiving diode R, linked, in the example described, to the communications interface 24.

In the example described, the incidences of the beams F1 and F2 on the front and rear face of the windscreen are above the limit incidence for which the beams are practically totally reflected by the faces of the windscreen, in the absence of humidity (misting and water droplets). In contrast, a part of these beams is lost by transmission towards the passenger compartment and/or the outside of the vehicle, in the presence of drops of water or of misting on the faces, and the quantity of light reflected and received by the receiving diode R reduces with the quantity of water on the windscreen.

In the embodiment represented in FIG. 2A, the module 20 includes two inserts I1 and I2 implanted, according to the invention, in the thickness of the windscreen, in particular between the glass panel 10a and the spacer film 11, and between the spacer film 11 and the glass panel 10b, respectively. In practice, the inserts I1 and I2 are produced in the form of metal plates, with a high coefficient of reflection. The respective outer surfaces S1 and S2 of the inserts I1 and I2 are in contact with the respective glass panels 10a and 10b. The surfaces S1 and S2 are reflecting, and form waveguides with the faces AV and AR of the windscreen.

Referring to FIG. 2, the emitting diode E1, electroluminescent in the example described, emits a beam F1 which undergoes a plurality of reflections between the surface S1 and the front face AV of the windscreen, advantageously in the thickness of the glass panel 10a. At least a part of the beam F1 reflected is finally detected by the receiving diode R.

The emitting diode E2, electroluminescent in the example described, emits a light beam F2 which undergoes a plurality of reflections between the reflecting surface S2 and the rear face AR of the windscreen. The beam F2 is finally detected by the receiving diode R.

In the embodiment represented in FIG. 2B, the module 20 advantageously includes a single insert I1. The beam F2 emitted by the diode E2 undergoes a plurality of reflections between the surface S12 of the insert I1 and the face AR of the windscreen. The optical indices of the glass panels and of the spacer 11 are very similar and the measurement of the beam part F2 received is practically undisturbed by the slight deflection due to the interface between the spacer 11 and the panel 10b.

Furthermore, the beam F1, emitted by the diode E1, undergoes a plurality of reflections between the surface S11 of the insert I1 and the surface AV of the glazing.

In a variant, provision may be made to use, as reflecting surface S1 and/or S2, an a thermal film implanted in the thickness e' of the spacer 11 of certain laminated windscreens. Such a film has the initial function of filtering radiation, by reflection, especially infrared radiation present in sunlight, with a view to preventing an undesirable temperature rise in the passenger compartment. The emission wavelengths of the emitting diodes E1 and E2 are preferably in the infrared range and the front and rear faces of the windscreen can guide the beams F1 and F2, by co-operation with such a film. In that context, the present invention also envisages the use of an a thermal film of this type, as a reflecting surface of a detection device according to the invention.

Advantageously, the beams F1 and F2 which the emitting diodes E1 and E2 emit respectively have luminous intensities which are modulated in different ways. In practice, the luminous intensities of the beams F1 and F2 are modulated by square waveforms, of different respective frequencies. The detection device advantageously includes a stage for demodulation on the basis of the respective square-wave frequencies, which makes it possible to distinguish the luminous intensities originating from the reflections on the front face from the luminous intensities originating from the reflections on the rear face of the windscreen. Furthermore, such a modulation of the intensity of the beams additionally makes it possible to distinguish these reflected lights from ambient light (sun, light in the passenger compartment, etc.).

The receiving diode R moreover advantageously contributes to the detection of ambient light on the windscreen (insolation, illumination by the headlights of a following vehicle, etc.).

In practice, predetermined luminous intensities of the reflected beams F1 and F2 respectively are detected in the absence of drops of water and/or of misting. By comparison with such predetermined intensities, the wiper system and/or the heating, ventilation and air-conditioning installation are triggered if a variation in the intensities of the reflected beams is detected.

In the embodiment represented in FIG. 2, the emitting diodes E1 and E2, as well as the receiving diode R are affixed onto the free surface (rear face AR) of the panel 10b, on the vehicle passenger-compartment side.

Referring now to FIG. 3A, a second embodiment of the present invention is described, in which the .emitting diodes E1 and E2 are implanted (embedded, if appropriate) in the thickness e' of the spacer film 11. The power supply for the electroluminescent diodes E1 and E2 is provided by the connection 21 to these diodes which, in the example represented, is also inserted into the thickness of the windscreen (between the film 11 and the panel 10a in the example represented).

In the example represented in FIG. 3A, the module includes two receiving diodes R1 and R2, also implanted into the thickness e' of the spacer film 11. In a variant, the module may include only one implanted receiving diode. According to another variant, this receiving diode can be a fixed to the rear face AR of the windscreen, as represented in FIG. 2.

In a variant of the second embodiment of the present invention, as represented in FIG. 3B, the module 20 advantageously includes a single insert I1 provided with two large reflecting surfaces S11 and S12 opposite the faces AV and AR of the windscreen, forming waveguides for the beams F1 and F2.

According to one more elaborate embodiment of the invention, the detection device furthermore includes a temperature sensor advantageously implanted into the thickness of the windscreen and configured to co-operate with the module 20 for detecting misting on the face AR, especially in order to adjust the temperature of the air to be blown in for de-misting the windscreen. In this embodiment, the temperature-mode sensor is preferably completely implanted into the spacer film 11, and advantageously in contact with one face of the front panel 10a (outside), so as directly to detect the outside temperature of the windscreen, in order to obtain a direct measurement in terms of temperature, on the outside of the windscreen.

Clearly, the present invention is not limited to the embodiment described above by way of example. It extends to other variants.

The device described in the above example advantageously includes two emitting diodes for detecting the presence of drops of water and of misting on the front and rear faces of the windscreen 1. In a simplified variant of this device, the module 20 includes only one emitting diode for detecting the presence of misting or of drops of water on the windscreen.

The emission incidence of the beams F1 and F2 is chosen above to be greater than the abovementioned limit incidence, which makes it possible advantageously to recover practically the whole of the beams emitted, at the receiving diode R, in the absence of drops of water and/or of misting on the windscreen. Although advantageous, such incidences are capable of variants.

The diodes, in the above example, emit optical waves. In a more general way, the module of the device includes means for emitting electromagnetic radiation, such as optical waves, or else radio-frequency or UHF waves, forming an electromagnetic beam capable of undergoing reflection on one face of the windscreen. More generally yet, the device according to the invention can be configured to carry out detection by electromagnetic means, for example, of radar or other signals.

It should be noted that the device according to the invention is, in a general way, configured so as to detect a parameter representative of a state associated with a motor vehicle, for example an external temperature or temperature in the passenger compartment, insolation of the vehicle, etc.

Provision may be made, moreover, to detect the presence of dust on the windscreen, for example on the basis of a measurement of reflection, of the type described above, from one chosen face of the windscreen. For example, a film of nicotine on the face AR of the windscreen may contribute to modifying the luminous intensity of the reflected beam F2, and can thus be detected by measuring the quantity of light reflected after de-misting of the windscreen, as appropriate.

Furthermore, in the example described above, the emitting diodes and the receiving diode or diodes are preferably placed on the same rear face AR (passenger compartment side) of the windscreen. In a variant, they may be placed on different front or rear faces of the windscreen.

In particular, provision may be made to arrange an emitting diode and a receiving diode substantially facing one another, or else side by side, if it is desired, in particular, to detect light returned by the windscreen, by diffusion. In this context, the misting and/or water droplets detection device according to the preferred embodiment of the invention includes means for receiving light returned, in a general way, by the windscreen, by reflection or else by diffusion.

It should be noted that the inserts I1 and I2 can be dispensed with in the variant of the water-droplets and demisting detection device as represented in FIG. 3A described above. This is because provision can be made to make each of the beams F1 and F2 undergo only a single reflection before being detected by the receiving diode or diodes R1 and R2. In particular, in the variant according to which the emitting diodes E1 and E2 are implanted into the thickness of the windscreen, provision can be made to arrange these diodes opposite the respective faces of the windscreen, and to have them surrounded, with the receiving diode or diodes, with a substantially opaque film in such a way that they illuminate substantially only the respective front and rear faces.

Needless to say, in the further developed embodiment described above, the sensor provided can detect any other parameter than just temperature. An outside-airspeed sensor may be provided, for example, for modeling, regulation and/or compensation of ventilation in the passenger compartment, for example.

The present invention also envisages a device for detection of illumination of the windscreen, especially by insolation. In one application to detection of this type, the module 20 includes an optical sensor implanted in the windscreen, preferably, in contact with the panel 10a forming its front face, in order directly to detect light on the windscreen.

The heterogeneous structure of the glazing 1 (spacer 11 between two panels 10a and 10b) is described above by way of example. In a variant, the glazing is produced in a solid material, while a sensor module is at least partly cast into its thickness.

The invention applies, moreover, to glazing formed by a stack of successive glass panels, alternating with transparent films. In order, for example, to detect a parameter representative of the state associated with the outer surface AV of the glazing, such as its temperature or water droplets, provision may be made to implant a sensor or a reflecting surface against the rear face (film side) of the panel which is in contact with the outside of the vehicle.

What is claimed is:

1. A device for detecting a parameter representative of a state associated with a glazing of a motor vehicle including a module (20), comprising:

means (E1, E2) for emitting at least one electromagnetic beam (F1) towards one face (AV) of the glazing, wherein said means for emitting are disposed within said glazing;

means (R) for receiving at least a part of the beam returned by said face; and at least one insert (I1, I2) at least partly implanted into a thickness (e) of the glazing, provided with a surface (S1, S2; S11) facing said face (AV, AR), said surface formed of a material that substantially reflects the beam (F1), in such a way that the beam, from emission to reception, undergoes a plurality of reflections in the thickness of the glazing, between the surface (S1, S2; S11) of the insert (I1) and the face (AV, AR) of the glazing, wherein said beam follows a path from said means for emitting to said one face of the glazing without passing through said insert, wherein the receiving means include at least one sensor for detecting said part of the beam returned by said face, and implanted into the thickness of the glazing, and wherein the emitting means are configured to emit a first electromagnetic beam intended to be at least partly returned by a front face of the glazing, as well as a second beam intended to be at least partly returned by a rear face of the glazing, with a view to detecting foreign substances on the front and/or rear faces of the glazing and the module includes at least one insert in the thickness of the glazing, equipped with a first reflecting surface facing the front face, and with a second reflecting surface facing the rear face, while the receiving means are configured to receive at least parts of the first and second beams, which are reflected respectively by the front and rear faces.

2. A device according to claim 1, wherein the emitting means include first and second sources suitable for emitting the said first and second beams respectively, while the receiving means include a sensor for detecting the reflected parts of the first and second beams; and in that the first and second sources, as well as the said sensor, are applied against the same face of the glazing.

3. A device for detecting at least one parameter representative of at least one state associated with a glazing of a motor vehicle, the device comprising:

a first emitting means (E1) for emitting a first, electromagnetic beam (F1) that is reflected by a first face (AV) of the glazing;

a second emitting means (E2) for emitting a second electromagnetic beam (F2) that is reflected by a second face (AR) of the glazing;

receiving means (R) for receiving at least a part of the first electromagnetic beam reflected by the first face and for receiving at least a part of the second electromagnetic beam reflected by the second face;

at least one insert (I1, I2) at least partly implanted into a thickness (e) of the glazing, the at least one insert comprising a first surface (S1; S11) facing the first face and a second surface (S2; S11) facing the second face, the first and second surfaces formed of a material that substantially reflects the first and second electromagnetic beams, in such a way that, from emission to reception, the first electromagnetic beam undergoes a first plurality of reflections in the glazing between the first surface of the at least one insert and the first face of the glazing, and the second electromagnetic beam undergoes a second plurality of reflections in the glazing between the second surface of the at least one insert and the second face of the glazing.

4. A device according to claim 3, wherein the first electromagnetic beam follows a first path from the first emitting means to the first face of the glazing without passing through the at least one insert, and wherein the second electromagnetic beam follows a second path from the second emitting means to the second face of the glazing without passing through the at least one insert.

5. A device according to claim 3, wherein at least one of the first emitting means and the second emitting means comprises an emitting source applied against the first face or the second face of the glazing.

6. A device according to claim 3, wherein at least one of the first emitting means and the second emitting means is implanted into the thickness e of the glazing.

7. A device according to claim 3, wherein both the first emitting means and the second emitting means are implanted into the thickness e of the glazing.

8. A device according to claim 3, wherein the receiving means comprise a first sensor (R1) for detecting the first electromagnetic beam reflected by the first face of the glazing, and a second sensor (R2) for detecting the second electromagnetic beam reflected by the second face of the glazing.

9. A device according to claim 8, wherein at least one of the first and second sensors is implanted into the thickness e of the glazing.

10. A device according to claim 3, wherein the first face comprises the front face of the glazing and the second face comprises the rear face of the glazing.

11. A device according to claim 3, wherein the at least one insert comprises a single insert (S11) having the first surface (S11) and the second surface (S12) opposite one another.

12. A device according to claim 3, wherein the at least one insert comprises a first insert (I1) and a second insert (I2) having the first surface (S1) and the second surface (S2), respectively.

13. A device according to claim 3, wherein the first emitting means and the second emitting means comprise first and second emitting sources, respectively, both of the first and second emitting sources being applied against one of the faces selected from the first face and the second face of the glazing.

14. A device according to claim 3, further comprising a luminous-flux sensor inserted into the thickness (e) of the glazing.

15. A device according to claim 3, wherein the first electromagnetic beam and the receiving means detect foreign substances on the first face.

16. A device according to claim 15, wherein the second electromagnetic beam and the receiving means detect foreign substances on the second face.

17. A device according to claim 16, wherein the first and second faces comprise the front and rear faces of an automobile windscreen, and wherein the foreign substances on the front and rear faces comprise water and mist, respectively.

18. A device for detecting at least one parameter representative of at least one state associated with a glazing of a motor vehicle, the glazing comprising first and second glass panels (10a, 10b) respectively having first and second outer faces (AV, AR) separated by a thickness (e) of the glazing, and a spacer 11 of thickness (e') interposed between the first and second glass panels, the device comprising:

a first emitting means (E1) for emitting a first electromagnetic beam (F1) that is reflected by the first face (AV) of the glazing;

a second emitting means (E2) for emitting a second electromagnetic beam (F2) that is reflected by the second face (AR) of the glazing;

receiving means (R) for receiving at least a part of the first electromagnetic beam reflected by the first face and for receiving at least a part of the second electromagnetic beam reflected by the second face (AR);

at least one insert (I1, I2) at least partly implanted into a thickness e of the glazing, the at least one insert comprising a first surface (S1; S11) substantially opposite the first face and a second surface (S2; S11) substantially opposite said second face, said first and second surfaces formed of a material that substantially reflects the first and second electromagnetic beams, in such a way that, from emission to reception, the first electromagnetic beam undergoes a first plurality of reflections in the glazing between the first surface of the at least one insert and the first face of the glazing, and the second electromagnetic beam undergoes a second plurality of reflections in the glazing between the second surface of the at least one insert and the second face of the glazing.

19. A device according to claim 18, wherein the first electromagnetic beam follows a first path from the first emitting means to the first face of the glazing without passing through the at least one insert, and wherein the second electromagnetic beam follows a second path from the second emitting means to the second face of the glazing without passing through the at least one insert.

20. A device according to claim 18, wherein at least one of the first emitting means and the second emitting means comprises an emitting source applied against the first face or the second face of the glazing.

21. A device according to claim 18, wherein at least one of the first emitting means and the second emitting means is implanted into the spacer of the glazing.

22. A device according to claim 18, wherein both the first emitting means and the second emitting means are implanted into the spacer of the glazing.

23. A device according to claim 18, wherein the receiving means comprise a first sensor (R1) for detecting the first electromagnetic beam reflected by the first face of the glazing, and a second sensor (R2) for detecting the second electromagnetic beam reflected by the second face of the glazing.

24. A device according to claim 23, wherein at least one of the first and second sensors is implanted into the spacer of the glazing.

25. A device according to claim 18, wherein the first face comprises the front face of the glazing and the second face comprises the rear face of the glazing.

26. A device according to claim 18, wherein the at least one insert comprises a single insert (I11) having the first surface (S11) and the second surface (S12) opposite one another.

27. A device according to claim 18, wherein the at least one insert comprises a first insert (I1) and a second insert (I2) having the first surface (S1) and the second surface (S2), respectively.

28. A device according to claim 18, wherein the first emitting means and the second emitting means comprise first and second emitting sources, respectively, both of the first and second emitting sources being applied against one of the first face and the second face of the glazing.

29. A device according to claim 18, further comprising a luminous-flux sensor inserted into the thickness (e) of the glazing.

30. A device according to claim 18, wherein the first electromagnetic beam and the receiving means detect foreign substances on the first face.

31. A device according to claim 30, wherein the second electromagnetic beam and the receiving means detect foreign substances on the second face.

32. A device according to claim 31, wherein the first and second faces comprise the front and rear faces of an automobile windscreen, and wherein the foreign substances on the front and rear faces comprise water and mist, respectively.

* * * * *